(12) United States Patent
Ciambecchini et al.

(10) Patent No.: US 8,049,031 B2
(45) Date of Patent: Nov. 1, 2011

(54) SOLID FORMS OF FESOTERODINE FUMARATE

(75) Inventors: Umberto Ciambecchini, Patrica (IT); Maurizio Zenoni, Patrica (IT); Stefano Turchetta, Patrica (IT)

(73) Assignee: Chemi S.p.A., Cinisello Balsamo (MI) (IT)

( * ) Notice: Subject to any disclaimer, the term of this patent is extended or adjusted under 35 U.S.C. 154(b) by 12 days.

(21) Appl. No.: 12/654,123

(22) Filed: Dec. 10, 2009

(65) Prior Publication Data
US 2010/0152483 A1 Jun. 17, 2010

(30) Foreign Application Priority Data
Dec. 10, 2008 (IT) .............................. MI2008A2176

(51) Int. Cl.
*C07C 67/02* (2006.01)
(52) U.S. Cl. ......... 560/250; 560/129; 560/136; 560/252
(58) Field of Classification Search .................... None
See application file for complete search history.

(56) References Cited

U.S. PATENT DOCUMENTS
6,858,650 B1 * 2/2005 Meese ........................ 514/530
2006/0014832 A1 1/2006 Breitenbach et al.

FOREIGN PATENT DOCUMENTS
WO WO 2007/140986 A1 12/2007
WO WO 2007/141298 A1 12/2007
WO WO 2009/044278 A1 4/2009

* cited by examiner

*Primary Examiner* — Sudhakar Katakam
(74) *Attorney, Agent, or Firm* — Lucas & Mercanti LLP.

(57) ABSTRACT

New solid forms of fesoterodine fumarate are described. In particular, amorphous fesoterodine fumarate, characterized by a powder X-ray diffraction spectrum as shown in FIG. 1 and by an IR spectrum as shown in FIG. 2 is described. Also fesoterodine fumarate in crystalline form I, characterized by a powder X-ray diffraction spectrum as shown in FIG. 3, by a DSC profile as shown in FIG. 4, by an IR spectrum as shown in FIG. 5, by a solid state $^{13}$C-NMR spectrum as shown in FIG. 6 and by a Raman spectrum as shown in FIGS. 7, 8 and 9 is described.

16 Claims, 9 Drawing Sheets

PXRD of amorphous fesoterodine fumarate

IR spectrum of amorphous fesoterodine fumarate

PXRD of fesoterodine fumarate form I

DSC of fesoterodine fumarate form I

IR spectrum of fesoterodine fumarate form I

13C-NMR spectrum of fesoterodine fumarate form I 3600-2500 cm$^{-1}$ Raman spectrum of fesoterodine fumarate form I 1800-910 cm⁻¹ Raman spectrum of fesoterodine fumarate form I 910-50 cm⁻¹ Raman spectrum of fesoterodine fumarate form I

SOLID FORMS OF FESOTERODINE FUMARATE

Fesoterodine fumarate is the international non-proprietary name (INN) of the active ingredient isobutyric acid 2-[(R)-3-diisopropylammonium-1-phenylpropyl)-4-(hydroxy-methyl) phenyl ester hydrogen fumarate, which can be represented by the structural formula shown in FIG. 1.

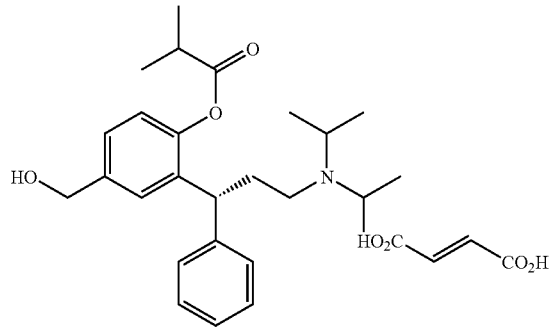

FIG. 1

Fesoterodine fumarate was approved in Europe and in the USA for the treatment of overactive bladder syndrome with the commercial name TOVIAZ®.

Fesoterodine fumarate was described for the first time in U.S. Pat. No. 6,858,650, where its crystallization from methyl ethyl ketone-cyclohexane is presented, obtaining colourless crystal flakes, having a melting point of 103° C.

WO2007140986 states that it is possible to obtain fesoterodine fumarate in crystalline form from just methyl ethyl ketone, but the details of such preparation are not made clear.

Given the need for fesoterodine fumarate in solid form, it has been attempted many times to obtain it by applying the method of crystallization of fesoterodine fumarate shown in U.S. Pat. No. 6,858,650, example 6 column 16, lines 39-65, but it has never been possible to isolate a solid, given that an oil always separates from the crystallization mixture, which does not change into a solid even after prolonged agitation into the crystallization mixture.

The same behaviour was observed when carrying out attempts at crystallization of fesoterodine fumarate from just methyl ethyl ketone, as indicated in WO2007140986 page 14, lines 25-28.

It is clear that there is a need to identify a simple method for obtaining fesoterodine fumarate in solid form and in particular in crystalline form.

During the course of studies aimed at identifying a method for obtaining fesoterodine fumarate in solid form it has been found that it is possible to subject aqueous fesoterodine fumarate solutions to lyophilisation and at the end of the process obtain fesoterodine fumarate in solid amorphous form.

Moreover, it has been found that amorphous solid fesoterodine fumarate can be suspended or dissolved in a solvent and that it is possible, after stirring as a suspension in the solvent or by reprecipitation from the solution, to obtain fesoterodine fumarate in crystalline form known as form I (method A), characterised hereafter.

It has thus also been found that from solutions of fesoterodine fumarate from which product in solid form is not precipitated even after prolonged stirring in solution and by cooling, it is possible to obtain fesoterodine fumarate in crystalline form known as form I, after starting the crystallization reaction through seeding of the solution with crystallization seeds of fesoterodine fumarate in form I (method B).

Figure 3:
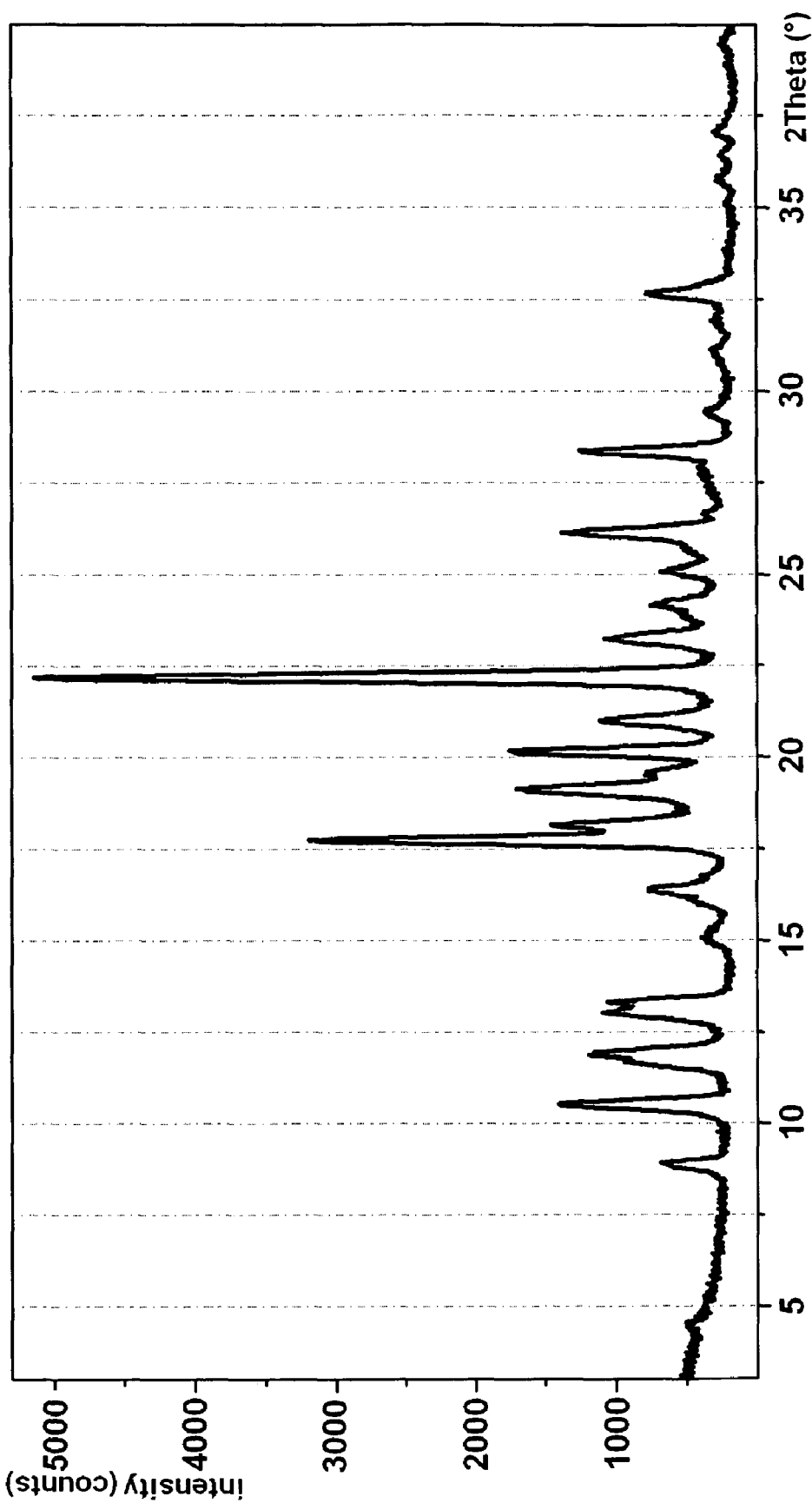
FIG. 3 shows the powder X-ray diffraction spectrum of fesoterodine fumarate in crystalline form 1.
Figure 4:
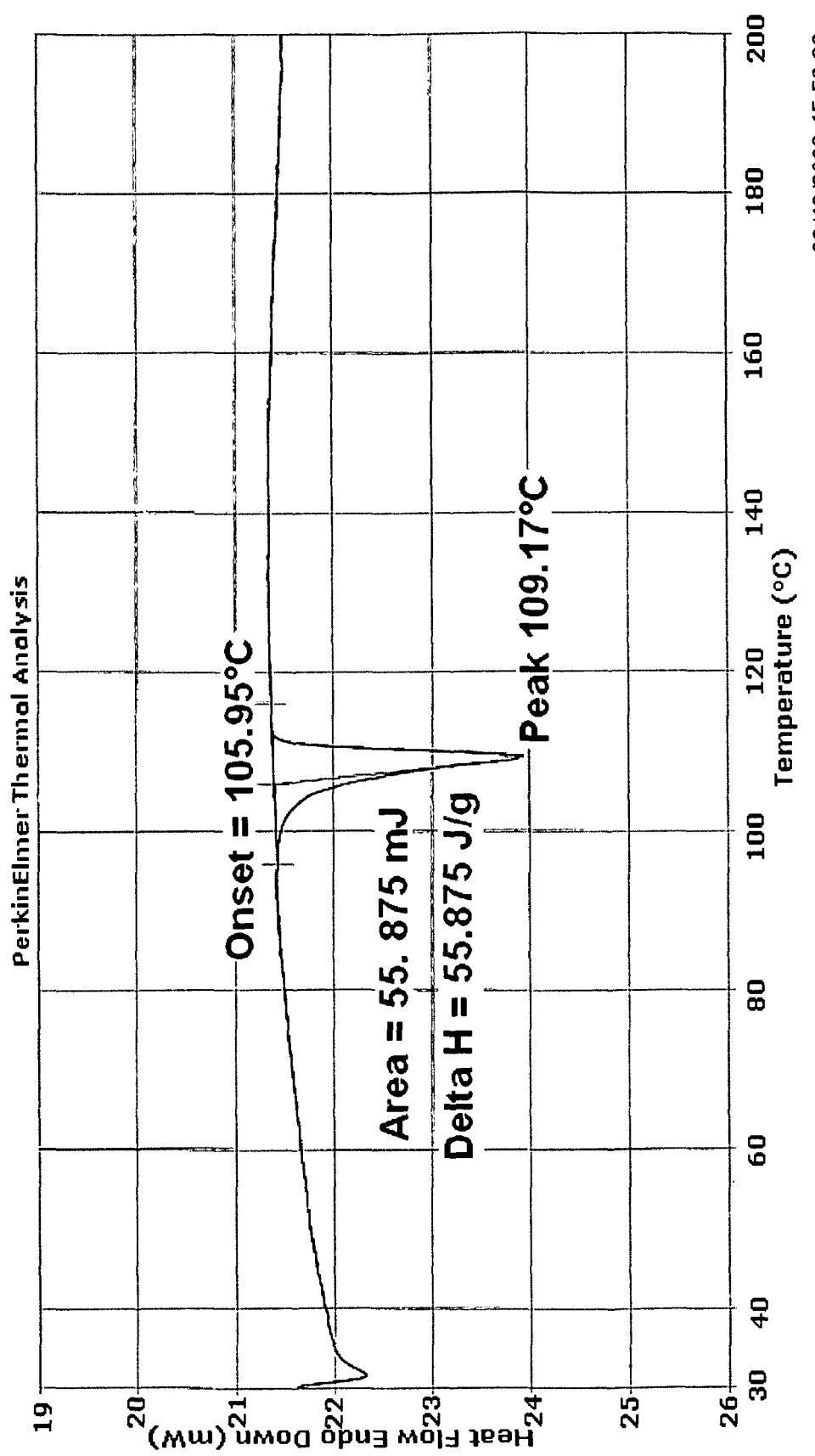
FIG. 4 shows the DSC profile of fesoterodine fumarate in crystalline form I.
Figure 5:
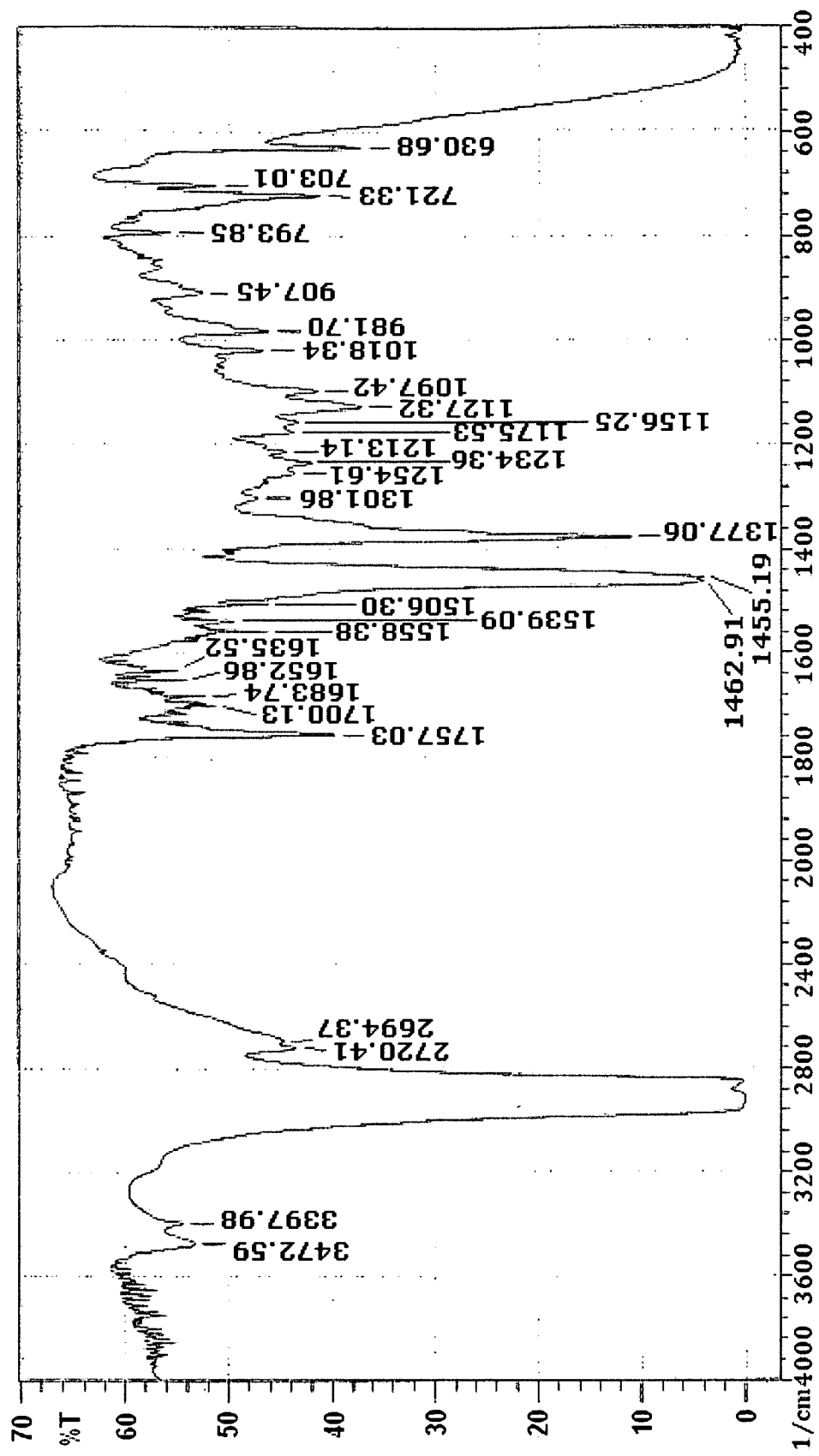
FIG. 5 shows the IR spectrum of fesoterodine fumarate in crystalline form I.
Figure 6:
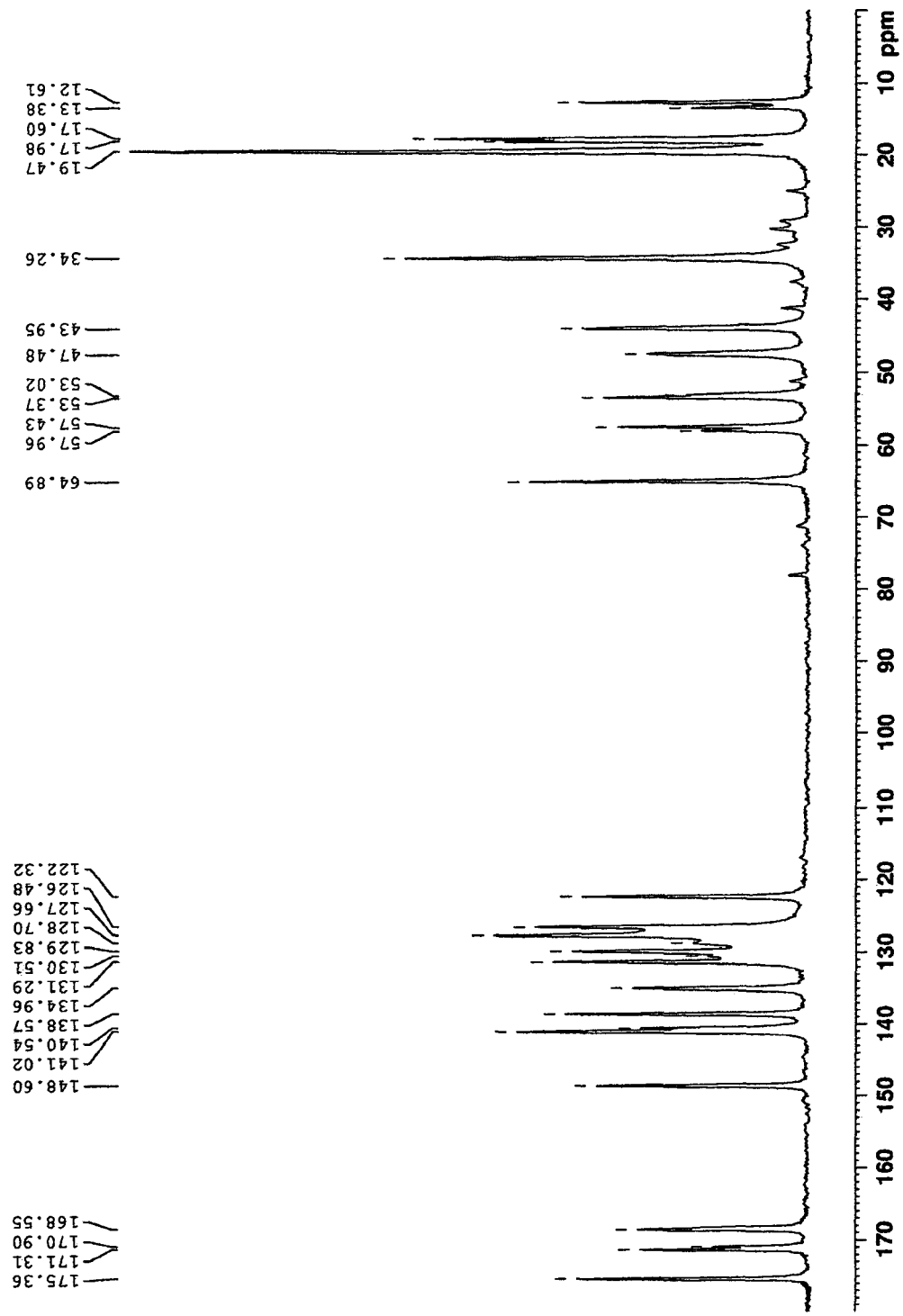
FIG. 6 shows the $^{13}$C-NMR spectrum of fesoterodine fumarate in crystalline form I.
Figure 7:
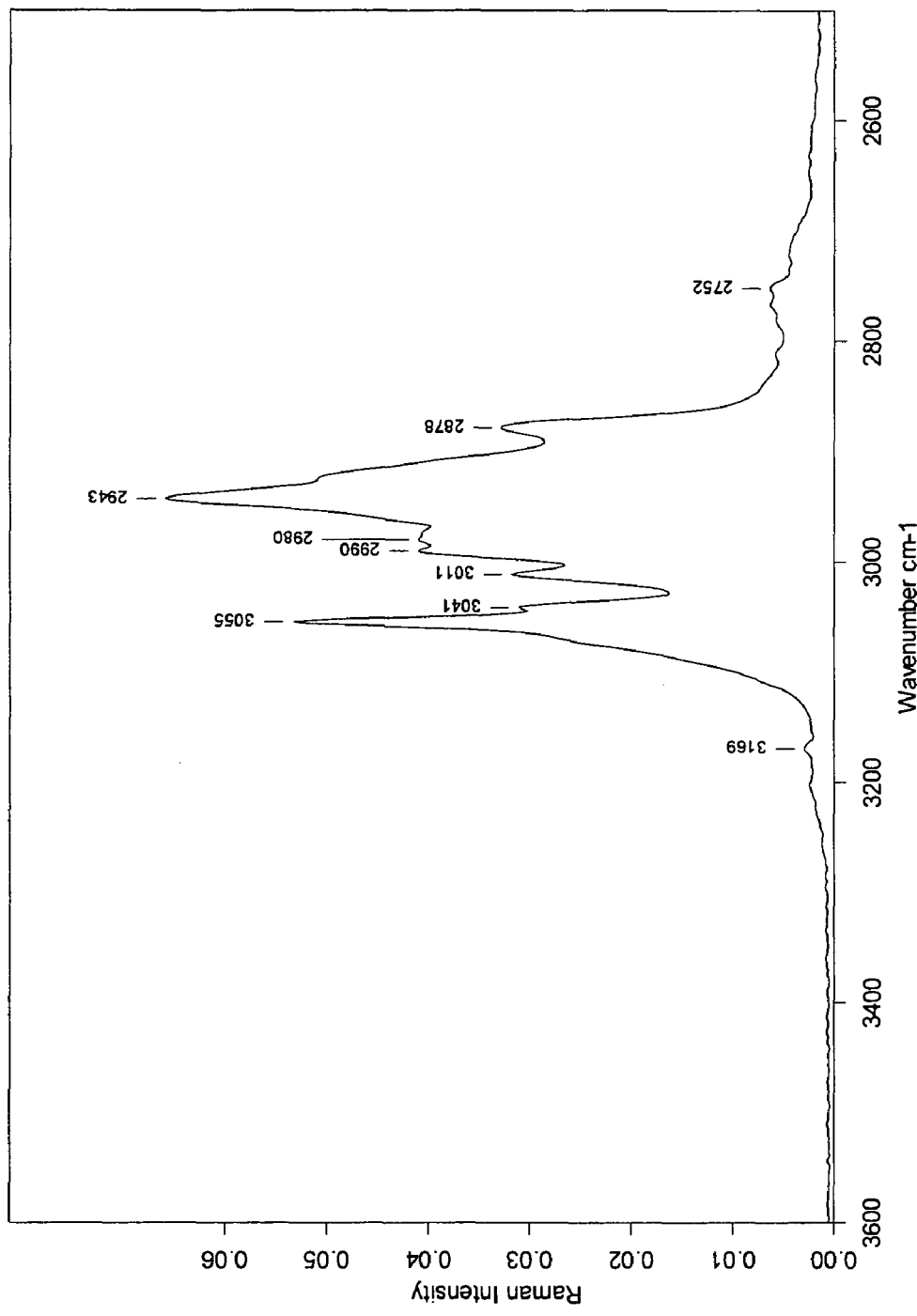
FIG. 7 shows the 3600-2500 cm$^{-1}$ Raman spectrum of fesoterodine fumarate in crystalline form I.
Figure 8:
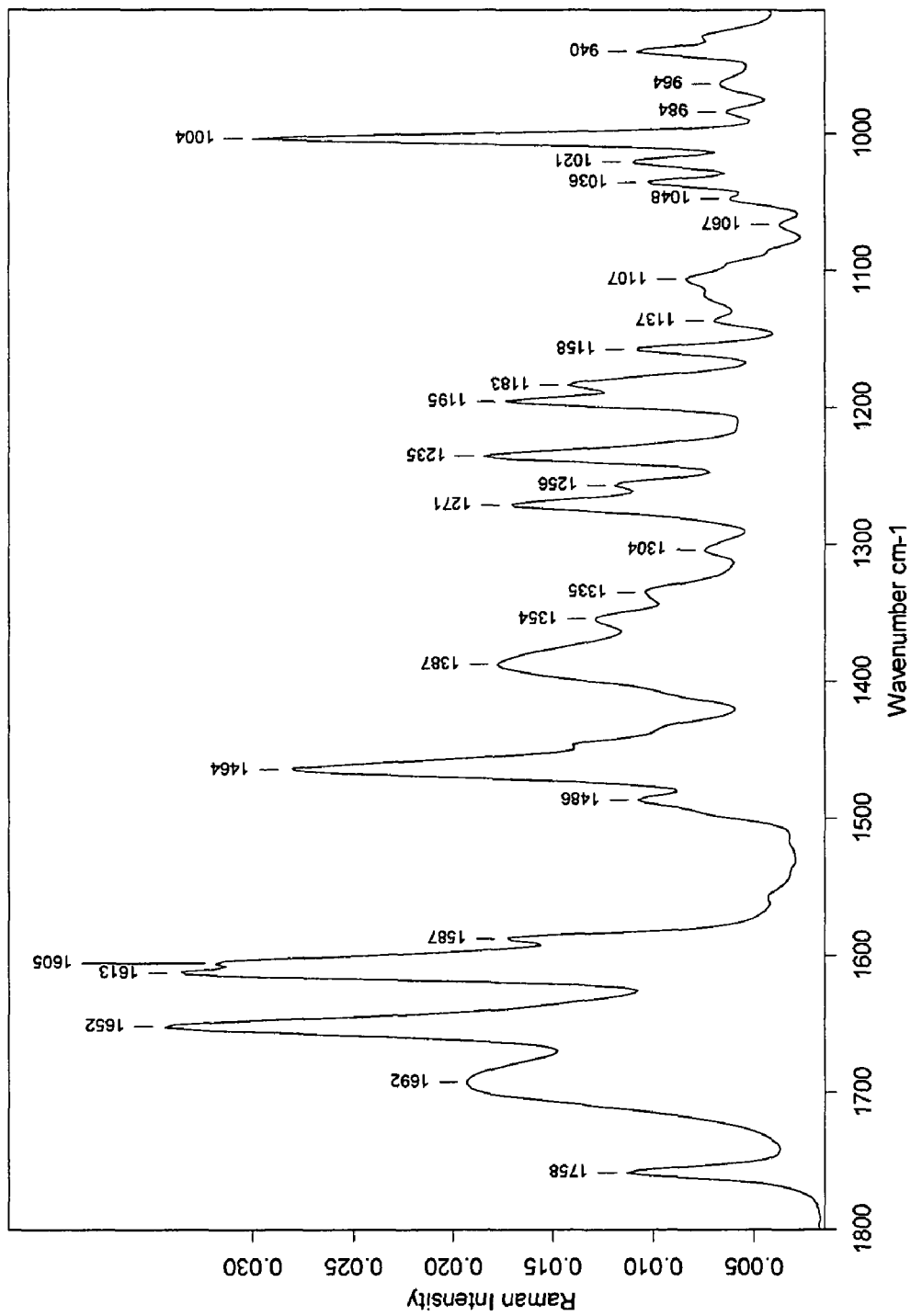
FIG. 8 shows the 1800-910 cm$^{-1}$ Raman spectrum of fesoterodine fumarate in crystalline form I.
Figure 9:
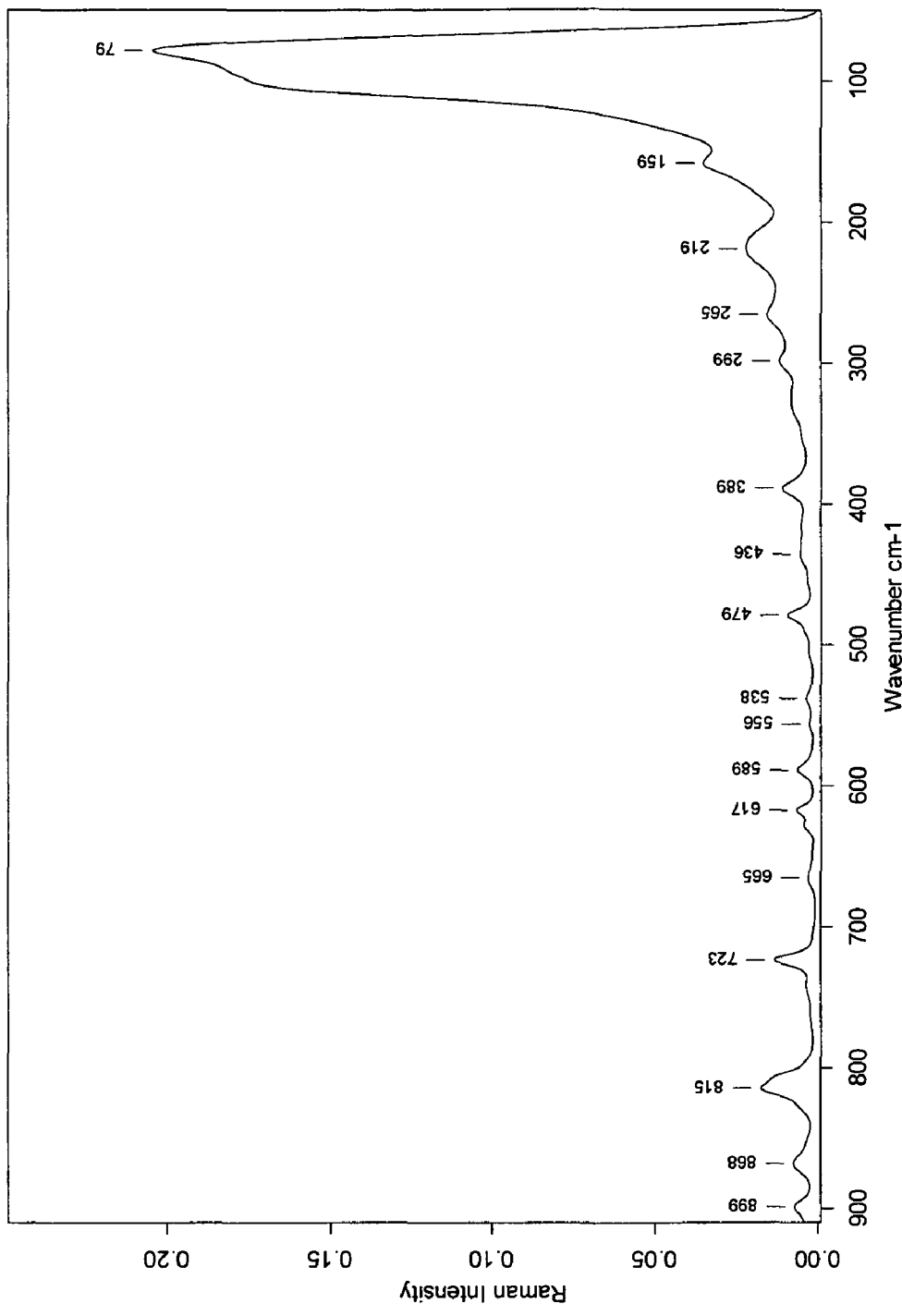
FIG. 9 shows the 910-50 cm$^{-1}$ Raman spectrum of fesoterodine fumarate in crystalline form I.

The object of the present invention is therefore fesoterodine fumarate in crystalline form I, characterised by the profile of the powder X-ray diffractogram (PXRD) shown in FIG. 3 and/or by the DSC profile shown in FIG. 4 and/or by the IR spectrum shown in FIG. 5, and/or by the $^{13}$C-NMR spectrum in solid state shown in FIG. 6 and/or by the Raman spectrum shown in FIGS. 7, 8 and 9. The characteristic peaks that distinguish the aforementioned PXRD, DSC, IR, $^{13}$C-NMR and Raman graphs are those shown hereafter.

The object of the present invention is also a process for the synthesis of fesoterodine fumarate in crystalline form I, comprising suspending amorphous fesoterodine fumarate in a solvent, solubilising the product, if necessary by heating, and crystallizing the product, if necessary by cooling (method A).

The object of the present invention is also a process for the synthesis of fesoterodine fumarate in crystalline form I, comprising preparing a solution of fesoterodine fumarate in a solvent and carrying out the seeding of the solution with seeds consisting of fesoterodine fumarate in crystalline form I to start crystallization (method B).

A further object of the present invention is also a process for the synthesis of amorphous fesoterodine fumarate, comprising subjecting an aqueous solution containing fesoterodine and about a molar equivalent of fumaric acid to lyophilisation.

Figure 1:
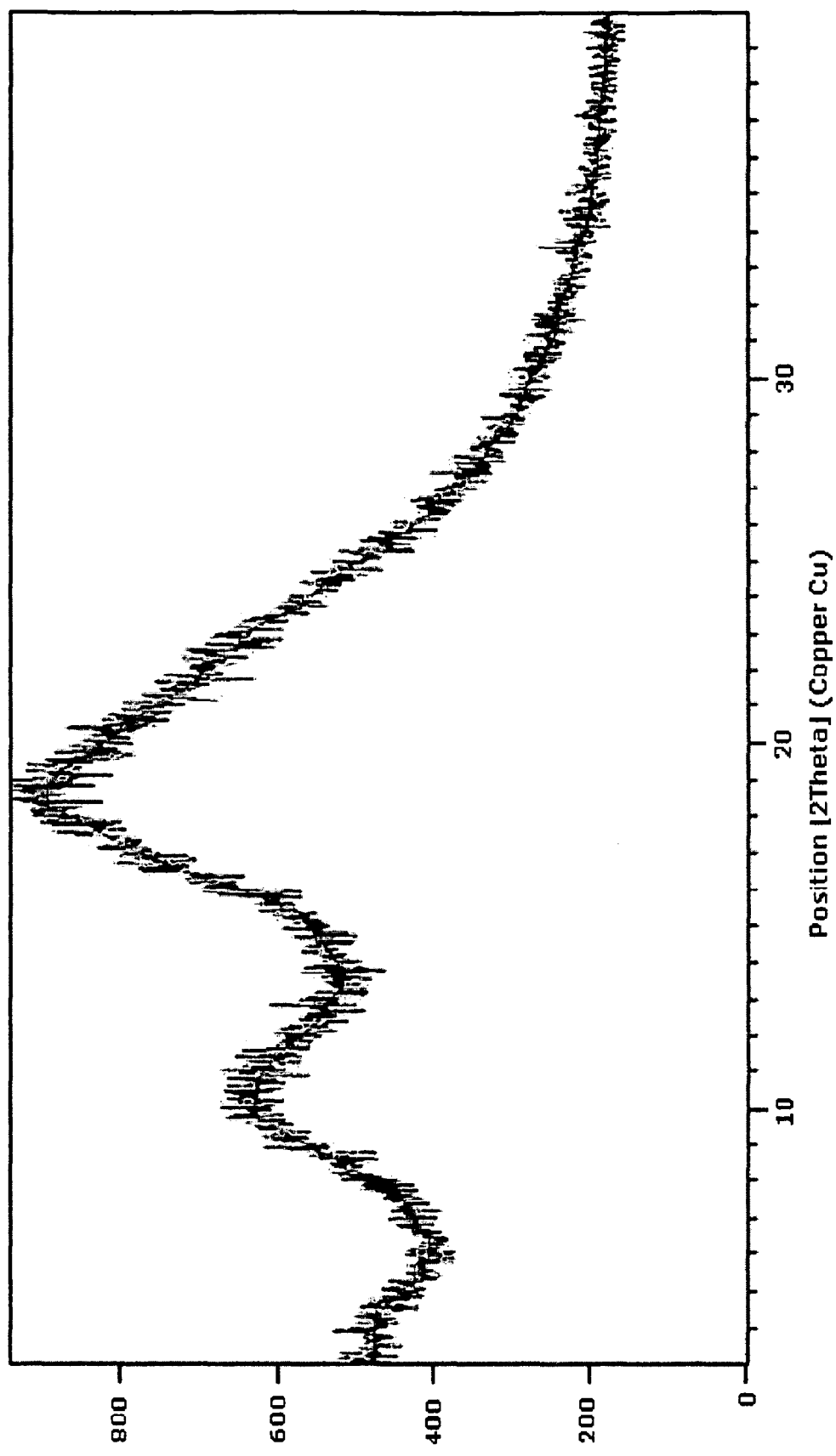
FIG. 1 shows the powder X-ray diffraction spectrum of amorphous fesoterodine fumarate.
Figure 2:
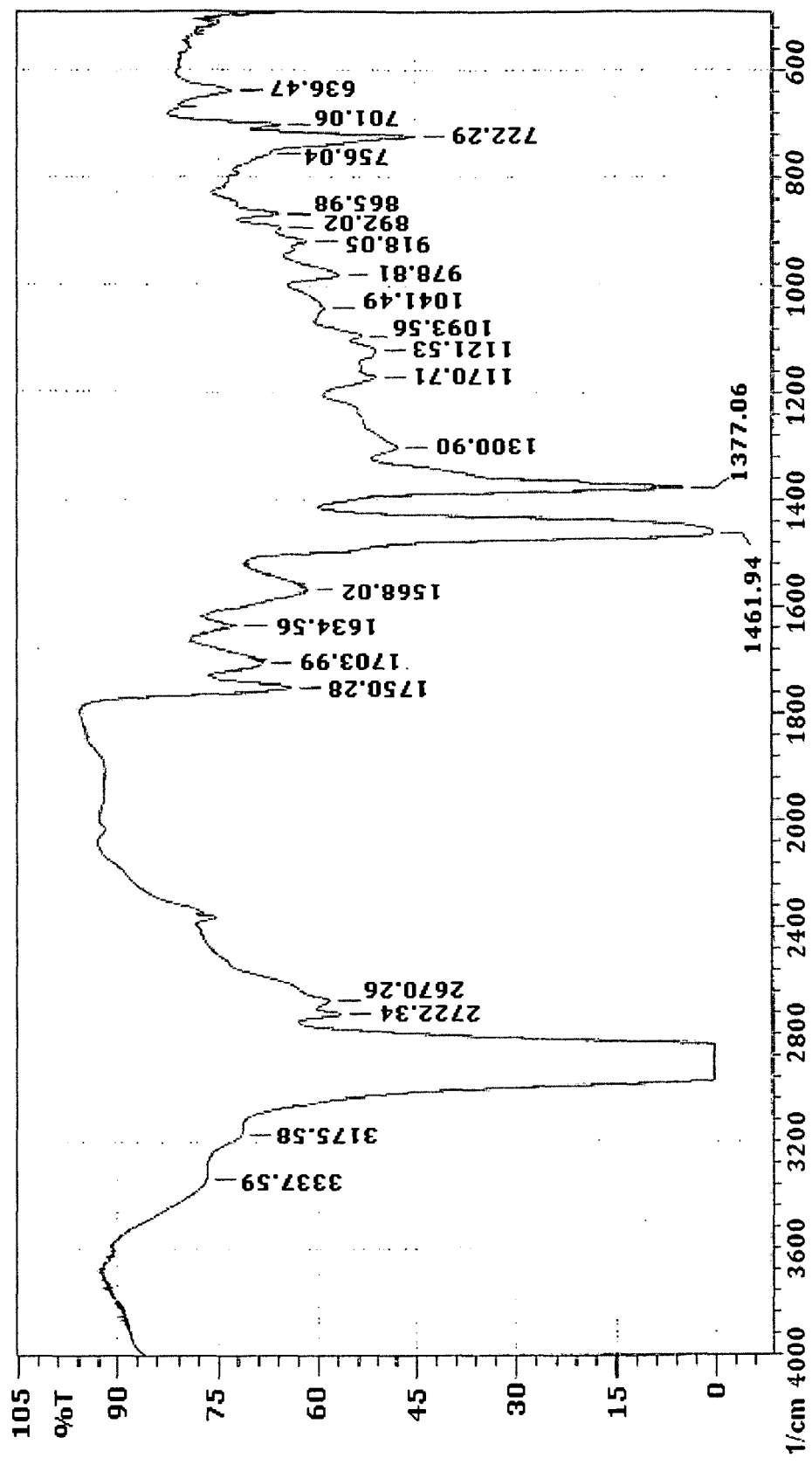
FIG. 2 shows the IR spectrum of amorphous fesoterodine fumarate.

The amorphous fesoterodine fumarate obtained with the process of the present invention is characterised by having a powder X-ray diffraction spectrum matching the one shown in FIG. 1 or having the IR spectrum as shown in FIG. 2, where the characteristic peaks of the profile are shown hereafter.

The object of the present invention also concerns pharmaceutical formulations comprising fesoterodine fumarate in crystalline form I, wherein such formulations are preferably solid and even more preferably in tablet form.

Amorphous fesoterodine fumarate is characterised by the profile of the powder X-ray diffractogram (PXRD) shown in FIG. 1 and by an IR spectrum as shown in FIG. 2 (dispersion in Nujol), whose characteristic peaks of the IR spectrum are found at the wavelengths: 3338; 3176; 2722; 2670; 1750; 1704; 1635; 1588; 1301; 1171; 1122; 1094; 1041; 979; 918; 892; 866; 701 cm$^{-1}$, with a margin for error on the indicated value for each peak off ±2 cm$^{-1}$.

The amorphous fesoterodine fumarate is prepared by subjecting a solution obtained by dissolving fesoterodine and fumaric acid in deionised water to lyophilisation. The aqueous solution subjected to lyophilisation contains fesoterodine and about a molar equivalent of fumaric acid.

Fesoterodine fumarate in crystalline form I is characterised by the profile of the powder X-ray diffractogram (PXRD) shown in FIG. 3, the characteristic peaks of which are found at positions 2 theta: 8.95; 10.55; 11.64; 11.94;13.02; 13.32; 15.01; 16.42; 17.74; 18.11; 19.14; 19.59; 20.16; 20.99; 22.20; 23.25; 24.16; 25.08; 26.13; 28.35; 32.66 degrees, with a margin for error on the indicated value for each peak off ±0.20 degrees (2 theta).

The following table shows further data that characterises the PXRD diffractogram of such a crystalline form.

TABLE 1

| Pos. [*2Th.] | Height [cts] | FWHM [*2Th.] | d-spacing [Å] | Rel. Int. [%] |
|---|---|---|---|---|
| 4.5045 | 91.83 | 0.2676 | 19.61710 | 1.95 |
| 8.9461 | 387.78 | 0.2342 | 9.88507 | 8.22 |
| 10.5553 | 1118.17 | 0.2007 | 8.38138 | 23.71 |
| 11.6395 | 647.12 | 0.2007 | 7.60301 | 13.72 |
| 11.9357 | 940.60 | 0.2007 | 7.41496 | 19.95 |
| 13.0169 | 835.08 | 0.2342 | 6.80138 | 17.71 |
| 13.3158 | 844.27 | 0.0669 | 6.64940 | 17.90 |
| 15.0099 | 138.95 | 0.2342 | 5.90252 | 2.95 |
| 16.4232 | 489.00 | 0.1171 | 5.39761 | 10.37 |
| 17.7442 | 2917.18 | 0.2342 | 4.99863 | 61.86 |
| 18.1089 | 1116.26 | 0.1171 | 4.89880 | 23.67 |
| 19.1434 | 1312.07 | 0.2509 | 4.63634 | 27.82 |
| 19.5937 | 441.86 | 0.1673 | 4.53079 | 9.37 |
| 20.0625 | 1153.11 | 0.1004 | 4.42597 | 24.45 |
| 20.1632 | 1416.92 | 0.0836 | 4.40407 | 30.05 |
| 20.9882 | 767.13 | 0.2676 | 4.23279 | 16.27 |
| 22.2051 | 4715.58 | 0.2342 | 4.00351 | 100.00 |
| 23.2542 | 713.56 | 0.3346 | 3.82521 | 15.13 |
| 24.1627 | 413.25 | 0.2007 | 3.68340 | 8.76 |
| 25.0754 | 347.02 | 0.2342 | 3.55136 | 7.36 |
| 26.1271 | 1088.50 | 0.1171 | 3.41075 | 23.08 |
| 28.3490 | 1011.58 | 0.1673 | 3.14828 | 21.45 |
| 29.4491 | 143.39 | 0.2676 | 3.03313 | 3.04 |
| 31.0790 | 107.19 | 0.2676 | 2.87768 | 2.27 |
| 31.9670 | 104.18 | 0.3346 | 2.79974 | 2.21 |
| 32.6603 | 584.70 | 0.1338 | 2.74187 | 12.40 |
| 35.8388 | 111.88 | 0.2342 | 2.50566 | 2.37 |
| 36.4629 | 94.36 | 0.2676 | 2.46419 | 2.00 |
| 37.0178 | 128.05 | 0.2342 | 2.42851 | 2.72 |

Fesoterodine fumarate in crystalline form I is characterised by the DSC profile shown in FIG. 4. In such a graph it is possible to see an endothermal peak due to the melting of the product with Peak onset at 105.95° C., Peak at 109.17° C. and melting enthalpy equal to 55.9 Joule/g.

Fesoterodine fumarate in crystalline form I is characterised by the IR spectrum shown in FIG. 5. (dispersion in Nujol) the characteristic peaks of which are encountered at the wavelengths: 3473; 1757; 1700; 1558; 1234; 1213; 1176; 1156; 1127; 1097; 1018; 982; 907; 794; 703 cm$^{-1}$, with a margin for error on the indicated value for each peak of ±2 cm$^{-1}$.

Fesoterodine fumarate in crystalline form I is characterised by the $^{13}$C-NMR spectrum in solid state shown in FIG. 6 the characteristic peaks of which are found at the frequencies: 175.36; 171.31; 170.90; 168.55; 148.60; 141.02; 140.54; 138.57; 134.96; 131.29; 130.51; 129.83; 128.70; 127.66; 126.48; 122.32; 64.89; 57.96; 57.43; 53.37; 53.02; 47.48; 43.95; 34.26; 19.47; 17.98; 17.60; 13.38; 12.61, with a margin for error on the indicated value for each peak of ±0.1 ppm.

Fesoterodine fumarate in crystalline form I is characterised by the Raman spectrum shown in FIGS. 7, 8 and 9, the characteristic peaks of which are found at the wavelengths: 3055; 3041; 2943; 2878; 1758; 1692; 1652; 1613; 1587; 1464; 1387; 1271; 1235; 1195; 1183; 1158; 1004; 815; 723 cm$^{-1}$, with a margin for error on the indicated value for each peak of ±2 cm$^{-1}$.

A process for the synthesis of fesoterodine fumarate in crystalline form I (method A), comprises suspending amorphous fesoterodine fumarate in a solvent, leaving the product to solubilise, if necessary by heating, with a heating rate ranging from 0.1 to 10° C./min, up until, in the cases in which the product does not melt at a lower temperature, the reflux temperature of the predetermined solvent and crystallizing the product, if necessary by cooling, carried out with a cooling speed ranging from 0.1 to 10° C./min up to a temperature at which at least 70% of the loaded product has precipitated, preferably a temperature of between 0 and 5° C. (method A). Preferably, the amorphous fesoterodine fumarate used in method A is prepared according to the process of the present invention.

Preferably, for the solvent alcohols $C_1$-$C_6$ are used and tert-amyl alcohol and isopropyl alcohol are particularly preferred.

Other solvents of particular interest are esters $C_1$-$C_4$ of carboxylic acids $C_1$-$C_4$, in particular ethyl acetate is preferred.

A further process for the synthesis of fesoterodine fumarate in crystalline form I (method B), comprises preparing a solution of fesoterodine fumarate in a solvent and carrying out the seeding of the solution with seeds consisting of fesoterodine fumarate in crystalline form I.

The seeds of fesoterodine fumarate in crystalline form I are preferably obtained by reprecipitation of fesoterodine fumarate according to method A.

The fesoterodine fumarate is suspended preferably in solvents in alcohols $C_1$-$C_6$, such as isopropyl alcohol, in ketones, such as methyl ethyl ketone, and/or in esters, such as ethyl acetate, then is solubilised by heating with a heating rate ranging from 0.1 to 10° C./min. until, in the cases in which the product does not solubilise at a lower temperature, the reflux temperature of the predetermined solvent and the crystallized product of fesoterodine fumarate in form I is obtained by cooling carried out with a cooling speed ranging from 0.1 to 10° C./min down to a temperature at which at least 70% of the product has precipitated, preferably to a temperature of between 0 and 5° C.

The following examples clarify in detail the conditions used to obtain the solid forms of fesoterodine fumarate, but they should not be taken to restrict the scope of protection of the present invention.

Experimental Part

The characterisation of fesoterodine fumarate in amorphous form and in crystalline form I has been carried out through the following spectroscopy techniques, in the experimental conditions listed below:

PXRD (Powder X Ray Diffraction)

| Experimental conditions | |
|---|---|
| Instrument type: | X'Pert PRO PANalytical |
| Measurement type | Single scan |
| Used wavelength | Cu Kα1 |
| Anode material: | Cu |
| X-ray tube Voltage (kV): | 40 |
| X-ray tube Current (mA): | 40 |
| Sample Movement type: | Spinning |
| Sample Rotation time (s): | 1.0 |

-continued

| Experimental conditions | |
|---|---|
| Filter Thickness (mm): | 0.020 |
| Filter Material: | Ni |
| Detector Name: | X'Celerator |
| Detector Type: | RTMS detector |
| Scan axis: | Gonio |
| Scan range (°): | 3.0000-39.9987 |
| Step size (°): | 0.0167 |
| No. of points: | 2214 |
| Scan mode: | Continuous |
| Counting time (s): | 12.700 |
| Application SW: | X'Pert Data Collector vs. 2.2d |
| Instrument control SW: | XPERT-PRO vs. 1.9B |
| Temperature | Room Temperature |

IR

| Experimental conditions | |
|---|---|
| Instrument type: | Shimadzu FTIR-8300 |
| Optical system | Single beam optics |
| Beam splitter | Germanium coated on KBr plate |
| Beam source | Ceramic |
| Detector | High sensitivity pyroelectric detector (DLATGS) |
| Wavenumber accuracy | ±0.25 cm$^{-1}$ |
| Sample preparation | 25% w/w dispersion in mineral oil (Nujol) |
| Temperature | Room temperature |

DSC

| Experimental conditions | |
|---|---|
| Instrument type: | Perkin Elmer DSC-7 |
| Calorimetric precision | better than ±0.1% |
| Temperature precision | ±0.1% |
| Temperature accuracy | ±0.1% |
| Heating rate | 10° C./min |
| Heating ramp | 30° C. to 250° C. |
| Sample preparation | 1 mg sample in a 50 µl capsule with holes |
| Thermal controller | TAC 7/ΔX |

Solid State NMR

| Experimental conditions | |
|---|---|
| Instrument type | Bruker Avance III |
| Magnetic field power | 400 MHz |
| Contact time | 1.5 ms |
| Rotation speed | 10 kHz |
| Temperature | Room temperature |

RAMAN

| Experimental conditions | |
|---|---|
| Instrument type | Bruker MultiRam FT-Raman |
| Detector setting | LN-Ge-Diode [external] |
| Source setting Laser | 9395.0 cm$^{-1}$; 1000 mV |
| Excitation source | Nd$^{3+}$-YAG Laser (1064 nm) |
| Source Configuration | backscattering (180°) |
| Raman Laser Power (mV) | 130 |
| Scanner velocity | 5 kHz |
| Apodization Function | Blackman-Harris 4-term |
| Phase resolution | 32.0000000 |
| Acquisition mode | Double sided, Forward-backward |
| Resolution | 4.0000000 |
| Raman Laser wavenumber | 9395.0000000 |
| Raman laser Power in mV | 1000.0000000 |

EXAMPLE 1

Preparation of Amorphous Fesoterodine Fumarate.

15.1 g (36.6 mmols) of fesoterodine are loaded into a 1 liter flask, followed by 4.25 g (36.6 mmols) of fumaric acid and 450 ml of deionised water. The mixture is stirred at 40° C. until complete dissolution of the solids and filtered over a 0.45 micron filter. The solution is then divided in equal parts and loaded into three 1000 ml flasks. Each flask is connected to a rotavapor without activating the vacuum and under rotation each flask is immersed in a dry ice and acetone bath kept at −50° C. Each flask is left in such conditions for two hours, until a uniform layer of frozen material is obtained on the inner surface of each flask. The three flasks are then connected to a lyophilisation apparatus CHRIST Alpha 1-4 LSC and their content is lyophilized. The conditions used were the following:

Conditioning
Coil Conditioning Temperature: −30° C.
Pump conditioning pressure: atmospheric.
Main Drying
Condenser temperature while drying: −50° C.
Residual pressure while drying: 0.25 mbar
Drying time: 16 hours.
External product temperature: 25° C.
Final Drying
Condenser temperature while drying: −50° C.
Residual pressure while drying: 0.02 mbar
Drying time: 13 hours.
External product temperature: 40° C.

At the end of the process a solid is discharged from the flask that is subjected to X-ray diffraction analysis.

The profile that is obtained is shown in FIG. 1 and it is the PXRD profile typical of an amorphous solid.

EXAMPLE 2

Preparation of Fesoterodine Fumarate in Crystalline Form I (Method A).

2 g of fesoterodine fumarate prepared according to example 1 are suspended in 10 ml of tert-amyl alcohol at 25° C. and kept under stirring for 4 hours in such conditions. The product initially solubilises to then precipitate in the form of a white solid.

The suspension is filtered over a Buchner and the solid residue is dried under vacuum at 50° C. for 12 hours, obtaining fesoterodine fumarate in crystalline form I.

EXAMPLE 3

Preparation of Fesoterodine Fumarate in Crystalline Form I (Method B).

To 27.3 g of fesoterodine dissolved in 160 ml of methyl ethyl ketone, 7.8 g of fumaric acid are added. The mixture is heated to 50° C., observing complete solution. The hot solution is filtered over Whatman filter paper and the solution is left to cool down to 18° C. At this temperature 100 mg of the product obtained from example 2 are added to the solution. A white solid is separated from the solution and the mixture is cooled further to 10° C. and kept in such condition for one hour and taken to 5° C. and kept at such a temperature for two hours. At the end the solid is filtered, washed with 2×30 ml of methyl ethyl ketone cooled to 5° C. and discharged to be dried. After drying under vacuum at 40° C. for 16 hours, 24 g of product consisting of fesoterodine fumarate is obtained, which is subjected to X-ray diffraction analysis. The diffractogram that is obtained matches the one shown in FIG. 2 (crystalline form I).

EXAMPLE 4

Preparation of Fesoterodine Fumarate in Crystalline Form I (Method B).

4 g of fesoterodine fumarate prepared according to example 1 are suspended in 10 ml of isopropyl alcohol at 25° C. and the suspension is heated to 60° C. with consequent dissolution of the suspended solid. The temperature is taken to 10° C. and 20 mg of product obtained from example 2 are added to the solution. The solution progressively becomes a slurry and is kept at 0÷10° C. for three hours, at the end of which the suspended product is filtered and washed with 5 ml of isopropanol at 10° C. The solid is dried under a vacuum at 50° C. for 12 hours, obtaining fesoterodine fumarate in crystalline form I.

EXAMPLE 5

Preparation of Fesoterodine Fumarate in Crystalline Form I (Method B)

2 g of fesoterodine fumarate prepared according to example 1 are suspended in 30 ml of ethyl acetate at 25° C. and the suspension is heated to 78° C. with consequent partial dissolution of the suspended solid that in part sticks to the walls in the form of oil. The temperature of the mixture is brought to 25° C. and 20 mg of product obtained from example 2 are added to it. The mixture progressively becomes a suspension of white solid product and is cooled to 0÷10° C. and kept in such conditions for one hour, at the end of which the suspended product is filtered and washed with 2×5 ml of ethyl acetate at 10° C. The solid is dried under a vacuum at 50° C. for 12 hours, obtaining 1.6 g of fesoterodine fumarate in crystalline form I.

The invention claimed is:

1. Fesoterodine fumarate in crystalline form I, characterized in that it has a powder X-ray diffraction spectrum having the following peaks (±0.20° 2 theta): 8.95; 10.55; 11.64; 11.94; 13.02; 13.32; 15.01; 16.42; 17.74; 18.11; 19.14; 19.59; 20.16; 20.99; 22.20; 23.25; 24.16; 25.08; 26.13; 28.35; 32.66° (2 theta); it has a DSC profile measured with a heating rate of 10° C./min that shows an endothermal peak with Peak onset at 105.95° C.±0.1° C., Peak at 109.17° C.±0.1° C. and it has an IR spectrum that shows the following peaks (±2 $cm^{-1}$): 3473; 1757; 1700; 1558; 1234; 1213; 1176; 1156; 1127; 1097; 1018; 982; 907; 794;703 $cm^{-1}$.

2. Fesoterodine fumarate in crystalline form I, according to claim 1, having $^{13}$C-NMR in solid state that shows the following peaks (±0.1 ppm): 175.36; 171.31; 170.90; 168.55; 148.60; 141.02; 140.54; 138.57; 134.96; 131.29; 130.51; 129.83; 128.70; 127.66; 126.48; 122.32; 64.89; 57.96; 57.43; 53.37; 53.02; 47.48; 43.95; 34.26; 19.47; 17.98; 17.60; 13.38; 12.61 ppm.

3. Fesoterodine fumarate in crystalline form I, according to claim 1, having a Raman spectrum that shows the following peaks (±2 $cm^{-1}$): 3055; 3041; 2943; 2878; 1758; 1692; 1652; 1613; 1587; 1464; 1387; 1271; 1235; 1195; 1183; 1158; 1004; 815; 723 $cm^{-1}$.

4. Process for obtaining fesoterodine fumarate in crystalline form I according to claim 1, comprising suspending amorphous fesoterodine fumarate in alcohols $C_1$-$C_6$ or esters $C_1$-$C_4$ of carboxylic acids $C_1$-$C_4$, solubilising the product and crystallizing the product.

5. Process according to claim 4, where the solubilization of the product is carried out by heating, preferably with a heating rate of between 0.1 and 10° C./min.

6. Process according to claim 5, where the heating is protracted until the reflux temperature of the solvent has been reached.

7. Process according to claim 4, wherein the crystallization of the product is obtained by cooling, preferably with a cooling speed of between 0.1 and 10° C./min.

8. Process according to claim 4, wherein the solvent is tert-amyl alcohol, isopropyl alcohol or ethyl acetate.

9. Process for obtaining fesoterodine fumarate in crystalline form I according to claim 1, comprising the preparation of a solution of fesoterodine fumarate in a solvent and starting the crystallization through seeding of the solution with crystallization seeds consisting of fesoterodine fumarate in crystalline form I.

10. Process according to claim 9, wherein the fesoterodine fumarate is solubilized by heating, preferably with a heating rate of between 0.1 and 10° C./min.

11. Process according to claim 10, wherein the heating is protracted until the reflux temperature of the solvent has been reached.

12. Process according to claim 9, also comprising the crystallization of fesoterodine fumarate by cooling, preferably with a cooling speed of between 0.1 and 10° C./min.

13. Process according to claim 9, wherein said solvent is selected among alcohols $C_1$-$C_6$ ketones, and/or esters, preferably among isopropyl alcohol, methyl ethyl ketone and/or ethyl acetate.

14. Process according to claim 9, wherein the seeds consisting of fesoterodine fumarate in crystalline form I are obtained according to the process of claim 4.

15. Solid pharmaceutical formulations comprising fesoterodine fumarate in crystalline form I of claim 1.

16. Pharmaceutical formulations according to claim 15 in tablet form.

* * * * *